United States Patent
Tanagi et al.

(10) Patent No.: US 11,919,877 B2
(45) Date of Patent: *Mar. 5, 2024

(54) PRODUCTION METHOD FOR 1,2,3,5,6-PENTATHIEPANE

(71) Applicant: MITSUBISHI GAS CHEMICAL COMPANY, INC., Tokyo (JP)

(72) Inventors: Hiroyuki Tanagi, Osaka (JP); Kouhei Takemura, Tokyo (JP); Hiroshi Horikoshi, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 820 days.

This patent is subject to a terminal disclaimer.

(21) Appl. No.: 16/980,030

(22) PCT Filed: Mar. 5, 2019

(86) PCT No.: PCT/JP2019/008642
§ 371 (c)(1),
(2) Date: Sep. 11, 2020

(87) PCT Pub. No.: WO2019/181484
PCT Pub. Date: Sep. 26, 2019

(65) Prior Publication Data
US 2021/0009553 A1    Jan. 14, 2021

(30) Foreign Application Priority Data
Mar. 22, 2018    (JP) ................. 2018-054403

(51) Int. Cl.
*C07D 341/00*    (2006.01)
*B01J 31/02*    (2006.01)

(52) U.S. Cl.
CPC ........ *C07D 341/00* (2013.01); *B01J 31/0239* (2013.01); *B01J 2531/98* (2013.01)

(58) Field of Classification Search
CPC .................................................. C07D 341/00
See application file for complete search history.

(56) References Cited

U.S. PATENT DOCUMENTS

| | | | |
|---|---|---|---|
| 3,488,362 A | 1/1970 | Morita et al. | |
| 5,041,240 A | 8/1991 | Green, II et al. | |
| 10,472,343 B2 * | 11/2019 | Tanagi | C07D 341/00 |
| 2002/0107338 A1 | 8/2002 | Wonmun et al. | |
| 2019/0040035 A1 | 2/2019 | Tanagi et al. | |

FOREIGN PATENT DOCUMENTS

| | | | |
|---|---|---|---|
| CN | 102260240 A | 11/2011 | |
| CN | 102351763 A | 2/2012 | |
| JP | 2002-293783 A | 10/2002 | |
| JP | 4573148 B2 | 11/2010 | |
| JP | 2014-198688 A | 10/2014 | |
| JP | 2017-165950 A | 9/2017 | |
| JP | 2018-135322 A | 8/2018 | |
| JP | 2018135322 * | 8/2018 | C07D 341/00 |
| WO | 2005/034974 A1 | 4/2005 | |
| WO | 2018/135417 A1 | 7/2018 | |

OTHER PUBLICATIONS

Banik, Molecules 2020, 25, 5918, 1-24.*
Halpern, Phase-Transfer Catalysis, 2012 Wiley-VCH Verlag Gmbh & Co. KGaA, Weinheim, pp. 495-501.*
Still, Ian. W. J. et al., "A simple, efficient synthesis of lenthionine and 1,2,4,6-Tetrathiepane from Dimethyl Disulfide", Tetrahedron Letters, vol. 22, No. 21, 1981, pp. 1939, 1940.
Liu, H. X. et al., "Improvement of Synthesis of Lenthionine", Specialty Petrochemicals, No. 1, 2005, pp. 21,22.
Hansen, H. C. et al., "Synthesis, Structure, and Reactions of Thiocarbonic Acid Derivatives: New Pentathiodipercarbonates, (RSS)$_2$C=S, a,a,a-Tris (Disulfide), and the First a,a,a-Tris (Trisulfide)", Tetrahedron, vol. 41, No. 22, 1985, pp. 5145-5158.
Liu, H. X. et al., "Synthesis and Thermal Analysis of Lenthionine", China Condiment, No. 9, 2005, pp. 25-27.
International Search Report issued in International Patent Application No. PCT/JP2019/008642, dated May 28, 2019 and English Translation thereof.
Supplementary European Search Report issued in EP 19 77 1047 dated Mar. 3, 2021.

* cited by examiner

*Primary Examiner* — Nizal S Chandrakumar
(74) *Attorney, Agent, or Firm* — GREENBLUM & BERNSTEIN, P.L.C.

(57) ABSTRACT

The present invention enables provision of a production method for 1,2,3,5,6-pentathiepane, the method comprising, in the following order, step A for reacting a trithiocarbonate, sulfur, and a methane dihalide together using a phase-transfer catalyst in a multilayer system having a water layer and an organic layer, step B for separating the water layer from the organic layer, and step C for stopping the reaction using an acid.

8 Claims, No Drawings

PRODUCTION METHOD FOR 1,2,3,5,6-PENTATHIEPANE

TECHNICAL FIELD

The present invention relates to a method for producing 1,2,3,5,6-pentathiepane.

BACKGROUND ART 1,2,3,5,6-Pentathiepane (hereinafter, lenthionine) is a compound that is useful for optical material applications and medical applications, and that has prospects for wide applications (Patent documents 1 and 2).

As a method for synthesizing lenthionine, a method that uses dimethyl disulfide as a starting material is known (Non-patent document 1). According to this method, the reaction results an oily solution containing lenthionine and thus purification by column chromatography is required, which is industrially disadvantageous. Moreover, it requires dimethyl disulfide which is industrially not easy to obtain as a raw material.

As another method for synthesizing lenthionine, a method in which diiodomethane and dibromomethane are reacted in an ethanol solvent, using sodium sulfide as a starting material is known (Non-patent document 2). Again, this method requires column chromatography for purification, which is industrially disadvantageous.

Generally, a disulfide bond or a trisulfide bond is known to be easily coupled and cleaved. Since lenthionine has a disulfide bond and a trisulfide bond, once these bonds are cleaved, polymerization progresses and results an insoluble polysulfide compound.

If an insoluble polysulfide compound is generated in large quantities in the reaction system, not only washing and thus industrialization becomes difficult, but also they are eventually mixed with lenthionine and thus makes high purity lenthionine difficult to obtain. Such polysulfide generation is making purification of lenthionine generated by known syntheses difficult.

PRIOR ART DOCUMENTS

Patent Documents

Patent document 1: Japanese Patent No. 4573148
Patent document 2: International Patent Application Publication WO2005/034974

Non-Patent Documents

Non-patent document 1: Tetrahedron.lett_1981_22_1939
Non-patent document 2: SPECIALTY PETROCHEMICALS, 2005, p. 22

SUMMARY OF THE INVENTION

Problems to be Solved by the Invention

The objective of the present invention is to provide a method for conveniently producing high purity lenthionine.

Means for Solving the Problems

The present inventors have gone through intensive studies, and as a result of which found that the above-described problem can be solved by carrying out reaction of trithiocarbonate, sulfur and methane dihalide in specific steps. Thus, the present invention is as follows.

[1] A method for producing 1,2,3,5,6-pentathiepane, the method comprising Steps A, B and C in this order:
 Step A: a step of carrying out reaction of trithiocarbonate, sulfur and methane dihalide using a phase-transfer catalyst in a multi-layer system having an aqueous layer and an organic layer;
 Step B: a step of separating the aqueous layer from the organic layer; and
 Step C: a step of terminating the reaction with an acid.

[2] The method for producing 1,2,3,5,6-pentathiepane according to [1], wherein the organic layer comprises one or more selected from the group consisting of benzene, toluene and tetrahydrofuran.

[3] The method for producing 1,2,3,5,6-pentathiepane according to [1], wherein the organic layer comprises toluene.

[4] The method for producing 1,2,3,5,6-pentathiepane according to any one of [1]-[3], wherein the phase-transfer catalyst comprises a quaternary alkylammonium salt.

[5] The method for producing 1,2,3,5,6-pentathiepane according to any one of [1]-[4], wherein the trithiocarbonate is disodium trithiocarbonate.

[6] The method for producing 1,2,3,5,6-pentathiepane according to any one of [1]-[5], wherein the methane dihalide comprises dibromomethane or diiodomethane.

[7] The method for producing 1,2,3,5,6-pentathiepane according to any one of [1]-[6], wherein the acid is sulfuric acid.

[8] The method for producing 1,2,3,5,6-pentathiepane according to any one of [1]-[7], wherein the multi-layer system is a two-layer system.

[9] The method for producing 1,2,3,5,6-pentathiepane according to any one of [1]-[8], wherein the mass ratio of water and an organic solvent used in a solvent is in a range of 30:70-50:50.

[10] The method for producing 1,2,3,5,6-pentathiepane according to any one of [1]-[9], wherein Steps A-C are carried out continuously.

Advantageous Effect of the Invention

According to the present invention, high purity lenthionine can readily be produced in good yield. Such high purity lenthionine can favorably be used for a variety of applications such as enhancing performance of an optical material.

EMBODIMENTS FOR CARRYING OUT THE INVENTION

A method for producing lenthionine according to the present invention comprises Steps A, B and C below:
 Step A: a step of carrying out reaction of trithiocarbonate, sulfur and methane dihalide using a phase-transfer catalyst in a multi-layer system having an aqueous layer and an organic layer;
 Step B: a step of separating the aqueous layer from the organic layer; and
 Step C: a step of terminating the reaction with an acid.

Although other steps may exist between Steps A-C, Steps A-C are to be carried out in this order.

Hereinafter, Steps A-C will be described in detail.

Step A: Step of Carrying Out Reaction of Trithiocarbonate, Sulfur and Methane Dihalide Using a Phase-Transfer Catalyst in a Multi-Layer System Having an Aqueous Layer and an Organic Layer Lenthionine is mainly synthesized in Step A. In order to synthesize lenthionine, first, trithiocarbonate is synthesized, and sulfur is allowed to react with the trithiocarbonate generated in the system to synthesize tetrathiocarbonate. Subsequently, methane dihalide is further added to allow reaction, thereby synthesizing lenthionine.

Trithiocarbonate

Trithiocarbonate used in the present invention is a compound represented by $M_2CS_3$ (where M is cationic species). Specific examples include disodium trithiocarbonate, dipotassium trithiocarbonate and dilithium trithiocarbonate. Among them, disodium trithiocarbonate is favorable due to its availability.

Trithiocarbonate can readily be obtained by reacting a sulfide salt and carbon disulfide in a solvent in the presence of a phase-transfer catalyst.

Specific examples of the sulfide salt include sodium sulfide, potassium sulfide and lithium sulfide.

The amount of carbon disulfide used is in a range of 0.5-1.5 molar equivalent to the sulfide salt, and preferably in a range of 0.8-1.2 molar equivalent from the viewpoint of suppressing progress of side reaction.

Phase Transfer Catalyst

The phase-transfer catalyst used in the present invention is a catalyst that is soluble in both water and an organic solvent, and one that is generally known may be used without limitation.

Specific examples include a quaternary phosphonium salt and a quaternary ammonium salt (preferably, a quaternary alkylammonium salt).

Examples of the quaternary phosphonium salt include tetraethylphosphonium chloride, tetraethylphosphonium bromide, tetraethylphosphonium iodide, tetrabutylphosphonium bromide, benzyltriphenylphosphonium bromide and tetraphenylphosphonium bromide.

Examples of the quaternary ammonium salt include tetramethylammonium hydroxide, tetraethylammonium hydroxide, benzyltrimethylammonium hydroxide, tetramethylammonium bromide, tetraethylammonium bromide, tetrabutylammonium bromide, benzyltrimethylammonium bromide, benzyltriethylammonium bromide, trimethylphenylammonium bromide, benzyltriethylammonium chloride, tetramethylammonium chloride, trioctylmethylammonium chloride, benzyltributylammonium chloride, benzyltrimethylammonium chloride, N-laurylpyridinium chloride, N-benzylpicolinium chloride, N-lauryl 4-picolinium chloride, N-laurylpicolinium chloride, tricaprylmethylammonium chloride, tetramethylammonium iodide, tetra-n-butylammonium iodide and tetrabutylammonium hydrogen sulfate.

While there is no limit to the amount of the phase-transfer catalyst used, it is preferably 0.01-10 mass % relative to the sulfide salt, and more preferably 0.05-5 mass % from the viewpoint of the reaction yield.

Solvent

The solvent used in the present invention contains water and an organic solvent, and is subjected to the reaction in a multi-layer state that results from phase separation. It is preferably in a two-layer state considering workability.

Any organic solvent can be used as long as it forms a separated layer from water and can dissolve methane dihalide. For example, hydrocarbon, aromatic hydrocarbon, an ether or ester solvent may be used. Among them, hydrocarbon, aromatic hydrocarbon or an ether solvent is preferable since the reaction yield of lenthionine is high and removal of the aqueous layer after the reaction is easy. A cyclic compound is more preferable, benzene, toluene or tetrahydrofuran is particularly preferable, and toluene is most preferable in terms of yield. Two or more of them may be used in combination.

The ratio between water and the organic solvent is in a range of 10:90-90:10 in mass ratio, and preferably in a range of 30:70-50:50 from the viewpoint of the reaction yield.

The amount of the solvent containing water and the organic solvent together is in a range of 1-40 times by mass relative to the sulfide salt, and preferably in a range of 2.0-20 times by mass from the viewpoint of production efficiency and reactivity.

The temperature of reaction between the sulfide salt and the carbon disulfide is usually in a range of $-10$-$60°$ C., and preferably in a range of 20-40° C. from the viewpoint of the reaction time and the reaction yield.

To the reaction solution containing trithiocarbonate resulting from the above-described reaction (which contains the multi-layer system having the aqueous layer and the organic layer, and the phase-transfer catalyst), sulfur is added to allow reaction therewith to give tetrathiocarbonate.

The amount of sulfur used is preferably in a range of 0.5-1.5 molar equivalent to the sulfide salt, and more preferably in a range of 0.8-1.2 molar equivalent from the viewpoint of suppressing progress of side reaction.

Methane Dihalide

Tetrathiocarbonate resulting from the above-described reaction is allowed to react with methane dihalide to synthesize lenthionine. Again, reaction takes place in this system in the presence of the multi-layer system having the aqueous layer and the organic layer, and the phase-transfer catalyst used above.

The methane dihalide used in the present invention is dichloromethane, dibromomethane, diiodomethane, bromochloromethane, chloroiodomethane or bromoiodomethane, preferably dibromomethane or diiodomethane from the viewpoint of reactivity, and particularly preferably dibromomethane.

The amount of methane dihalide used is preferably in a range of 0.5-1.5 molar equivalent to the sulfide salt, and more preferably in a range of 0.8-1.2 molar equivalent from the viewpoint of suppressing progress of side reaction.

The temperature of reaction between tetrathiocarbonate and methane dihalide is preferably in a range of $-10$-$60°$ C., and more preferably in a range of 10-40° C. As long as the reaction takes place in this range, progress of the reaction and suppression of the side reaction can be balanced.

Step B: Step of Separating the Aqueous Layer from the Organic Layer

The aqueous layer and the organic layer used in Step B are those obtained in Step A, where the reaction solution can be used directly from Step A. Moreover, Step B has to be carried out prior to the step of terminating the reaction with an acid (Step C). By conducting these steps in this order, insoluble matters generated through the reaction with the acid can be substantially reduced.

In Step B, the reaction solution resulting from the reaction in Step A is left to stand still until the solution is separated into layers, and then only the organic layer is collected. For example, a separating funnel may be used to remove only the aqueous layer from the reaction solution resulting from Step A.

Step C: Step of Terminating the Reaction with an Acid

Step C is a step of terminating the reaction by adding an acid to the organic layer collected in Step B. While any acid can be used as long as it is acidic, inexpensive sulfuric acid, hydrochloric acid, nitric acid, phosphoric acid or an aqueous solution thereof may favorably be used from an industrial point of view, where sulfuric acid is preferable for it allows rapid termination of the reaction, is nonvolatile and is highly safe.

After Step C, purification may be conducted by a known procedure such as liquid separation, crystallization operation or column chromatography. For example, the organic layer separated from the reaction solution may be subjected to a liquid separation operation to further concentrate the organic solvent so as to ease acquirement of high purity lenthionine by a crystallization operation. A crystallization operation may be carried out, for example, at a lenthionine concentration in a range of 5.0-40 mass % and at a temperature of −10-10° C. to acquire high purity lenthionine with good recovery rate.

EXAMPLES

Hereinafter, the present invention will be described specifically by way of examples, although these embodiments can suitably altered as long as the advantage of the present invention is exerted.

Method for Analyzing Lenthionine

A liquid chromatograph was used for analysis, with an ODS column (column: VP-ODS, Chemicals Evaluation and Research Institute, Japan, column size 4.6φ×150 mm).

A RI detector was used to calculate the production yield of lenthionine based on the mole ratio of dibromomethane as the raw material.

Conditions for Liquid Chromatograph

Oven temperature: 40° C.
Eluent: acetonitrile/distilled water (volume ratio)=50/50
Preparation of solution: 5 mg of sample was diluted with 10 ml of 0.1% formic acid solution (acetonitrile solvent) to be used as an analysis sample.

Method for Measuring Amount of Polysulfide Compound

While lenthionine is highly soluble in toluene, a polysulfide compound is not highly soluble in toluene. Accordingly, solids found in the system after quenching were collected by filtration, to which 50 ml of toluene was added. The resultant was further washed with water, and the insoluble matters in toluene were collected by filtration to be subjected to mass measurement.

Example 1

30.0 g (384 mmol) of sodium sulfide was dissolved in 100 g of water to prepare an aqueous solution. After 100 g of toluene and 1.24 g (3.84 mmol, 1 mol %) of tetrabutylammonium bromide as a phase-transfer catalyst were added, 29.2 g (384 mmol) of carbon disulfide was dropped therein to allow reaction at 20° C. for an hour, thereby preparing disodium trithiocarbonate.

To the resulting reaction solution, 12.3 g (384 mmol) of sulfur was added to further allow reaction at 20° C. for an hour, whereafter the solution was cooled to 0° C. Subsequently, 66.8 g (384 mmol) of dibromomethane was dropped to allow reaction for 20 hours. The amount of lenthionine generated after 20 hours of reaction was 28 mol %. Thereafter, the aqueous layer of the reaction solution was removed to separate the organic layer. To this organic layer, 100 g of an aqueous 1N sulfuric acid solution was added to perform quenching. After the quenching, the aqueous layer was discarded, and the resultant was further washed with 100 ml of ion exchanged water for three times. After the washing, the resultant was concentrated with an evaporator until the mass of the organic layer became 54 g, which was then crystallized at −2° C. to collect 7.2 g of lenthionine with a purity of 98% (isolation yield: 20%). No polysulfide compound was confirmed in the respective steps.

Example 2

An operation was carried out in the same manner as Example 1 except that the phase-transfer catalyst was changed from tetrabutylammonium bromide to tetrabutylammonium chloride. The amount of lenthionine generated after 20 hours of reaction was 24 mol %. The amount of lenthionine after the crystallization was 6.0 g (purity 98%: isolation yield 16.7%). No polysulfide compound was confirmed in the respective steps.

Comparative Example 1

Lenthionine was synthesized according to a Chinese reference (CHINA CONDIMENT, September, 2005, No 9, p 25).

5.9 g (76 mmol) of sodium sulfide was dissolved in 67 g of ethanol, to which 5.8 g (76 mmol) of carbon disulfide was added to allow reaction at 35° C. for 20 minutes. To the resulting reaction solution, 2.4 g (76 mmol) of sulfur was added, and the resultant was further allowed to react 35° C. for an hour, thereby preparing an ethanol solution of sodium tetrathiocarbonate.

18 g of ethanol was added to 13.2 g (76 mmol) of dibromomethane for dilution. The ethanol solution of dibromomethane was dropped to the previously prepared ethanol solution of sodium tetrathiocarbonate to allow reaction at 35° C. The amount of lenthionine generated after 20 hours of reaction was 4 mol %. After 20 hours, 100 g of an aqueous 1N sulfuric acid solution was added for quenching, and then extraction was conducted with 100 ml of toluene. Thereafter, the resultant was washed with 100 ml of ion exchanged water for three times. The residue after the solvent was distill away with an evaporator was a yellow oily compound, and when 100 g of toluene was added thereto, insoluble components were generated in large quantities. The mass of the insoluble component was 2.1 g, which was confirmed to be a polysulfide compound by IR measurement.

When crystallization operation was carried out in the same manner as Example 1, the crude crystal contained the polysulfide component as impurities and thus high purity product was not obtained due to difficulty in removal of the impurities by crystallization. Instead, yellow crystal was obtained (purity 80%).

Comparative Example 2

5.9 g (76 mmol) of sodium sulfide was dissolved in 120 g of ethanol, to which 5.8 g (76 mmol) of carbon disulfide was added to allow reaction at 35° C. for 20 minutes. 2.4 g (76 mmol) of sulfur was added to the resulting reaction solution to further allow reaction at 35° C. for an hour, thereby preparing an ethanol solution of sodium tetrathiocarbonate.

302 g of ethanol was added to 13.2 g (76 mmol) of dibromomethane for dilution. The previously prepared ethanol solution of sodium tetrathiocarbonate was dropped to the ethanol solution of dibromomethane to allow reaction at 35° C. The amount of lenthionine generated after 20 hours of reaction was 23 mol %. After 20 hours, 100 g of an aqueous 1N sulfuric acid solution was added for quenching, and then extraction was conducted by adding 100 g of toluene. Thereafter, the resultant was washed with 100 ml of ion exchanged water for three times. When 100 g of toluene was added after the solvent was distill away with an evaporator, insoluble components were generated. Thus, high purity product was not obtained by crystallization. The mass of the polysulfide compound insoluble in toluene was 2.3 g.

Comparative Example 3

5.9 g (76 mmol) of sodium sulfide was dissolved in 30 g of water, to which 83 g of toluene was added. 5.8 g (76 mmol) of carbon disulfide was dropped therein and the resultant was agitated at 35° C. for an hour. 2.4 g (76 mmol) of sulfur was added and further agitated at 35° C. for an hour.

13.2 g (76 mmol) of dibromomethane was dropped into the resultant to allow reaction at 35° C. As a result, the amount of lenthionine generated was 3 mol % after 3 hours, and 9 mol % after 20 hours. Since the yield was low, purification by crystallization was impossible.

The invention claimed is:

1. A method for producing 1,2,3,5,6-pentathiepane, the method comprising Steps A, B and C in this order:
    Step A: reacting trithiocarbonate, sulfur and methane dihalide using a phase-transfer catalyst in a multi-layer system having an aqueous layer and an organic layer, wherein the multi-layer system is a two-layer system;
    Step B: separating the aqueous layer from the organic layer; and
    Step C: terminating the reaction with an acid,
    wherein the method further comprises purifying 1,2,3,5,6-pentathiepane from the organic layer, after step C.

2. The method for producing 1,2,3,5,6-pentathiepane according to claim 1, wherein the organic layer comprises one or more selected from the group consisting of benzene and toluene and tetrahydrofuran.

3. The method for producing 1,2,3,5,6-pentathiepane according to claim 1, wherein the organic layer comprises toluene.

4. The method for producing 1,2,3,5,6-pentathiepane according to claim 1, wherein the phase-transfer catalyst comprises a quaternary alkylammonium salt.

5. The method for producing 1,2,3,5,6-pentathiepane according to claim 1, wherein the trithiocarbonate is disodium trithiocarbonate.

6. The method for producing 1,2,3,5,6-pentathiepane according to claim 1, wherein the methane dihalide comprises dibromomethane or diiodomethane.

7. The method for producing 1,2,3,5,6-pentathiepane according to claim 1, wherein the acid is sulfuric acid.

8. The method for producing 1,2,3,5,6-pentathiepane according to claim 1, wherein the mass ratio of water and an organic solvent used in a solvent is in a range of 30:70-50:50.

* * * * *